United States Patent
de Arruda et al.

(10) Patent No.: US 12,376,554 B2
(45) Date of Patent: Aug. 5, 2025

(54) HYBRID TOMATO PLANT NAMED RED CORAL

(71) Applicant: HM.CLAUSE, Inc., Davis, CA (US)

(72) Inventors: Marcio Pais de Arruda, Davis, CA (US); Michael Kuehn, Esparto, CA (US)

(73) Assignee: HM.CLAUSE, INC., Davis, CA (US)

( * ) Notice: Subject to any disclaimer, the term of this patent is extended or adjusted under 35 U.S.C. 154(b) by 316 days.

(21) Appl. No.: 17/867,112

(22) Filed: Jul. 18, 2022

(65) Prior Publication Data

US 2024/0016113 A1    Jan. 18, 2024

(51) Int. Cl.
*A01H 6/82* (2018.01)
*A01H 5/08* (2018.01)

(52) U.S. Cl.
CPC ............. *A01H 6/825* (2018.05); *A01H 5/08* (2013.01)

(58) Field of Classification Search
CPC .................................................... A01H 6/825
See application file for complete search history.

(56) References Cited

U.S. PATENT DOCUMENTS

| | | |
|---|---|---|
| 5,304,719 A | 4/1994 | Segebart |
| 5,367,109 A | 11/1994 | Segebart |
| 5,523,520 A | 6/1996 | Hunsperger et al. |
| 5,850,009 A | 12/1998 | Kevern |
| 5,968,830 A | 10/1999 | Dan et al. |
| 6,861,580 B2 | 3/2005 | Kuehn et al. |
| 9,309,533 B2 | 4/2016 | Hotzev |
| 9,402,356 B2 | 8/2016 | Jiang |
| 9,661,811 B2 | 5/2017 | Jiang |
| 9,968,044 B2 | 5/2018 | Jiang |
| 9,968,045 B2 | 5/2018 | Jiang |
| 9,968,046 B2 | 5/2018 | Jiang |
| 10,231,396 B2 | 3/2019 | Jiang |
| 10,238,050 B2 | 3/2019 | Jiang |
| 10,238,051 B2 | 3/2019 | Jiang |
| 10,238,052 B2 | 3/2019 | Jiang |
| 10,244,694 B2 | 4/2019 | Jiang |
| 10,257,991 B1 | 4/2019 | Darrigues |
| 10,257,992 B1 | 4/2019 | Kuehn |
| 10,271,511 B2 | 4/2019 | Martinez |
| 10,292,347 B2 | 5/2019 | Jiang |
| 10,321,640 B2 | 6/2019 | Martinez |
| 10,729,083 B2 | 8/2020 | Jiang |
| 10,743,487 B2 | 8/2020 | Jiang |
| 11,197,456 B2 | 12/2021 | Kuehn et al. |
| 11,202,436 B1 | 12/2021 | Martinez |
| 11,202,437 B1 | 12/2021 | Martinez |
| 11,304,396 B2 | 4/2022 | Martinez |
| 11,304,397 B2 | 4/2022 | Martinez |
| 11,344,002 B1 | 5/2022 | Kuehn et al. |
| 2016/0000028 A1 | 1/2016 | Jiang |
| 2016/0242375 A1 | 8/2016 | Jiang |
| 2016/0242376 A1 | 8/2016 | Jiang |
| 2016/0242377 A1 | 8/2016 | Jiang |
| 2019/0029206 A1 | 1/2019 | Kuehn |
| 2021/0040903 A1 | 2/2021 | Ninomiya |
| 2021/0040905 A1 | 2/2021 | Glugla et al. |
| 2021/0329875 A1 | 10/2021 | Martinez |
| 2021/0400902 A1 | 12/2021 | Martinez |
| 2021/0400904 A1 | 12/2021 | Martinez |

OTHER PUBLICATIONS

Stein and Rodriguez Rodeo Tomato for 2021—Ruby Crush PLANTanswers Bexar County AgriLife Extension Service, Texas A&M University (Year: 2024).*
Allard, 1960. Principle of Plant Breeding. John Wiley & Sons, Inc. p. 55.
Darnell, et al., 1990. DNA Replication, Repair and Recombination. In Molecular Cell Biology, 2nd edition, W.H. Freeman and Co., p. 478-487.
Eshed, et al., 1996. Less-Than-Additive Epistatic Interactions of Quatitative Trait Loci in Tomato. Genetics 143:1807-1817.
Poehlman, J.M. and Sleeper, D.A., Methods in Plant Breeding. In Breeding Field Crops, 5th ed. (2006), Iowa State University Press, pp. 171-183.
Sakata, Ruby Crush (Hybrid), retrieved on Oct. 18, 2022, from https://sakatavegetables.com/vegetable/tomato/tomato-grape-determinate/ruby-crush/, 2 pages.

* cited by examiner

*Primary Examiner* — David H Kruse

(74) *Attorney, Agent, or Firm* — McKee, Voorhees & Sease, PLC

(57) ABSTRACT

A novel hybrid tomato plant, designated RED CORAL is disclosed. The disclosure relates to the seeds of hybrid tomato designated RED CORAL, to the plants and plant parts of hybrid tomato designated RED CORAL, and to methods for producing a tomato plant by crossing the hybrid tomato RED CORAL with itself or another tomato plant.

23 Claims, No Drawings

HYBRID TOMATO PLANT NAMED RED CORAL

TECHNICAL FIELD

The present disclosure relates to the field of agriculture, to new and distinctive hybrid tomato plants, such as a hybrid plant designated RED CORAL and to methods of making and using such hybrids.

BACKGROUND

Tomato is an important and valuable vegetable crop. Thus, a continuing goal of plant breeders is to develop stable, high yielding tomato hybrids that are agronomically sound or unique. The reasons for this goal are to maximize the amount of fruit produced on the land used (yield) as well as to improve the fruit appearance, the fruit shape and size, eating and processing qualities and/or the plant agronomic and horticultural qualities. To accomplish this goal, the tomato breeder must select and develop tomato plants that have the traits that result in superior parental lines that combine to produce superior hybrids.

SUMMARY

The following embodiments and aspects thereof are described in conjunction with systems, tools and methods which are meant to be exemplary, not limiting in scope.

According to the disclosure, in some embodiments there is provided a novel hybrid tomato designated RED CORAL, also interchangeably referred to as 'hybrid tomato RED CORAL', 'tomato hybrid RED CORAL' or 'RED CORAL'.

This disclosure thus relates to the seeds of hybrid tomato designated RED CORAL, to the plants or parts of hybrid tomato designated RED CORAL, to plants or parts thereof comprising all of the physiological and morphological characteristics of hybrid tomato designated RED CORAL or parts thereof, and/or having all of the physiological and morphological characteristics of hybrid tomato designated RED CORAL, and/or having one or more of or all of the characteristics of hybrid tomato designated RED CORAL including but not limited to as determined at the 5% significance level when grown in the same environmental conditions, and/or having one or more of the physiological and morphological characteristics of hybrid tomato designated RED CORAL including but not limited to as determined at the 5% significance level when grown in the same environmental conditions and/or having all of the physiological and morphological characteristics of hybrid tomato designated RED CORAL including but not limited to as determined at the 5% significance level when grown in the same environmental conditions and/or having one or more of the physiological and morphological characteristics of hybrid tomato designated RED CORAL when grown in the same environmental conditions and/or having all of the physiological and morphological characteristics of hybrid tomato designated RED CORAL when grown in the same environmental conditions. The disclosure also relates to variants, mutants and trivial modifications of the seed or plant of hybrid tomato designated RED CORAL. In some embodiments, a representative sample of seed of hybrid tomato designated RED CORAL is deposited under NCIMB No. 44216.

Plant parts of the hybrid tomato plant designated RED CORAL of the present disclosure are also provided, such as, but not limited to, a scion, a rootstock, a fruit, a leaf, a flower, a peduncle, a stalk, a root, a stamen, an anther, a pistil, a pollen or an ovule obtained from the hybrid plant. The present disclosure provides fruit of the hybrid tomato plant designated RED CORAL of the present disclosure. Such fruit and parts thereof could be used as fresh products for consumption or in processes resulting in processed products such as food products comprising one or more harvested parts of the hybrid tomato designated RED CORAL, such as prepared fruit or parts thereof, canned fruit or parts thereof, freeze-dried or frozen fruits or parts thereof, diced fruits, juices, prepared fruit cuts, canned tomatoes, pastes, sauces, purees, catsups and the like. All such products are part of the present disclosure and the like. The harvested parts or food products can be or can comprise hybrid tomato fruit from hybrid tomato designated RED CORAL. The food products might have undergone one or more processing steps such as, but not limited to cutting, washing, mixing, frizzing, canning, etc. All such products are part of the present disclosure. The present disclosure also provides plant parts or cells of the hybrid tomato plant designated RED CORAL, wherein a plant regenerated from said plants parts or cells has one or more of, or all the phenotypic and morphological characteristics of hybrid tomato designated RED CORAL, such as one or more of or all the characteristics of hybrid tomato plant designated RED CORAL deposited under NCIMB No. 44216, including but not limited to as determined at the 5% significance level when grown in the same environmental conditions. All such parts and cells of the hybrid tomato RED CORAL are part of the present disclosure.

The plants and seeds of the present disclosure include those that may be of an essentially derived variety as defined in section 41 (3) of the Plant Variety Protection Act of The United States of America, e.g., a variety that is predominantly derived from hybrid tomato designated RED CORAL or from a variety that i) is predominantly derived from hybrid tomato designated RED CORAL, while retaining the expression of the essential characteristics that result from the genotype or combination of genotypes of hybrid tomato designated RED CORAL; ii) is clearly distinguishable from hybrid tomato designated RED CORAL; and iii) except for differences that result from the act of derivation, conforms to the initial variety in the expression of the essential characteristics that result from the genotype or combination of genotypes of the hybrid tomato plant designated RED CORAL.

In another aspect, the present disclosure provides regenerable cells. In some embodiments, the regenerable cells are for use in tissue culture of hybrid tomato designated RED CORAL. In some embodiments, the tissue culture is capable of regenerating plants comprising all of the physiological and morphological characteristics of hybrid tomato designated RED CORAL, and/or having all of the physiological and morphological characteristics of hybrid tomato designated RED CORAL, and/or having one or more of the physiological and morphological characteristics of hybrid tomato designated RED CORAL, and/or having the characteristics of hybrid tomato designated RED CORAL. In some embodiments, the regenerated plants have the characteristics of hybrid tomato designated RED CORAL including but not limited to as determined at the 5% significance level when grown in the same environmental conditions and/or have all of the physiological and morphological characteristics of hybrid tomato designated RED CORAL including but not limited to as determined at the 5% significance level when grown in the same environmental conditions and/or have one or more of the physiological and morphological characteristics hybrid tomato designated RED CORAL including but not limited to as determined at the 5% significance level when grown in the same environmental conditions and/or have all of the physiological and morphological characteristics of hybrid tomato designated RED CORAL when grown in the same environmental conditions.

In some embodiments, the plant parts and cells used to produce such tissue cultures will be embryos, meristematic cells, seeds, callus, pollens, leaves, anthers, pistils, stamens, roots, root tips, stems, petioles, fruits, cotyledons, hypocotyls, ovaries, seed coats, fruits, stalks, endosperms, flowers, axillary buds or the like. Protoplasts produced from such tissue culture are also included in the present disclosure. The tomato leaves, shoots, roots and whole plants regenerated from the tissue culture, as well as the fruits produced by said regenerated plants are also part of the disclosure. In some embodiments, the whole plants regenerated from the tissue culture have one, more than one, or all of the physiological and morphological characteristics of tomato hybrid designated RED CORAL, including but not limited to as determined at the 5% significance level when grown in the same environmental conditions.

The disclosure also provides for methods for vegetatively propagating a plant of the present disclosure. In the present application, vegetatively propagating can be interchangeably used with vegetative reproduction. In some embodiments, the methods comprise collecting parts of a hybrid tomato designated RED CORAL and regenerating a plant from said parts. In some embodiments, one of the parts can be for example a stem. In some embodiments, the parts can be used, for example, for a stem cutting that is rooted into an appropriate medium according to techniques known by the one skilled in the art. Plants and parts thereof, including but not limited to fruits thereof, produced by such methods are also included in the present disclosure. In another aspect, the plants and parts thereof such as stems and fruits produced by such methods comprise all of the physiological and morphological characteristics of hybrid tomato designated RED CORAL, and/or have all of the physiological and morphological characteristics of hybrid tomato designated RED CORAL and/or have the physiological and morphological characteristics of hybrid tomato designated RED CORAL and/or have one or more of the characteristics of hybrid tomato designated RED CORAL. In some embodiments, plants, parts or fruits thereof produced by such methods consist of one, more than one, or all of the physiological and morphological characteristics of tomato hybrid designated RED CORAL, including but not limited to as determined at the 5% significance level when grown in the same environmental conditions.

Further included in the disclosure are methods for producing fruits and/or seeds from the hybrid tomato designated RED CORAL. In some embodiments, the methods comprise growing a hybrid tomato designated RED CORAL to produce tomato fruits and/or seeds. In some embodiments, the methods further comprise harvesting the hybrid tomato fruits and/or seeds. Such fruits and/or seeds are parts of the present disclosure. In some embodiments, such fruits and/or seeds have all of the physiological and morphological characteristics of the fruits and/or seeds of hybrid tomato designated RED CORAL (e.g. those listed in Table 1 and/or deposited under NCIMB No. 44216) when grown in the same environmental conditions and/or have one or more of the physiological and morphological characteristics of the fruits and/or seeds of the hybrid tomato designated RED CORAL (e.g. those listed in Table 1 and/or deposited under NCIMB No. 44216) when grown in the same environmental conditions and/or have the characteristics of the fruits and/or seeds of the hybrid tomato designated RED CORAL (e.g. those listed in Table 1 and/or deposited under NCIMB No. 44216) when grown in the same environmental conditions.

Also included in this disclosure are methods for producing a tomato plant. In some embodiments, the tomato plant is produced by crossing the hybrid tomato designated RED CORAL with itself or other tomato plant. In some embodiments, the other plant can be a hybrid tomato other than the hybrid tomato designated RED CORAL. In other embodiments, the other plant can be a tomato inbred line. When crossed with an inbred line, in some embodiments, a "three-way cross" is produced. When crossed with itself (i.e. when a tomato RED CORAL is crossed with another hybrid tomato RED CORAL plant or when self-pollinated), or with another, different hybrid tomato, in some embodiments, a "four-way" cross is produced. Such three and four-way hybrid seeds and plants produced by growing said three and four-way hybrid seeds are included in the present disclosure. Methods for producing a three and four-way hybrid tomato seeds comprising (a) crossing hybrid tomato designated RED CORAL tomato plant with a different tomato inbred line or hybrid and (b) harvesting the resultant hybrid tomato seed are also part of the disclosure. The hybrid tomato seeds produced by the method comprising crossing hybrid tomato designated RED CORAL tomato plant with a different tomato plant such as a tomato inbred line or hybrid, and harvesting the resultant hybrid tomato seed are included in the disclosure, as are included the hybrid tomato plant or parts thereof and seeds produced by said grown hybrid tomato plants.

Further included in the disclosure are methods for producing tomato seeds and plants made thereof. In some embodiments, the methods comprise self-pollinating the hybrid tomato designated RED CORAL and harvesting the resultant hybrid seeds. Tomato seeds produced by such method are also part of the disclosure.

In another embodiment, this disclosure relates to methods for producing a hybrid tomato designated RED CORAL from a collection of seeds.

In some embodiments, the collection contains both seeds of inbred parent line(s) of hybrid tomato designated RED CORAL seeds and hybrid seeds of RED CORAL. Such a collection of seeds might be a commercial bag of seeds. In some embodiments, said methods comprise planting the collection of seeds. When planted, the collection of seeds will produce inbred parent lines of hybrid tomato RED CORAL and hybrid plants from the hybrid seeds of RED CORAL. In some embodiments, said inbred parent lines of hybrid tomato designated RED CORAL plants are identified as having a decreased vigor compared to the other plants (i.e. hybrid plants) grown from the collection of seeds. In some embodiments, said decreased vigor is due to the inbreeding depression effect and can be identified for example by a less vigorous appearance for vegetative and/or reproductive characteristics including a shorter plant height, small fruit size, fruit shape, fruit color or other characteristics. In some embodiments, seeds of the inbred parent lines of the hybrid tomato RED CORAL are collected and, if new inbred parent plants thereof are grown and crossed in a controlled manner with each other, the hybrid tomato RED CORAL will be recreated.

This disclosure also relates to methods for producing other tomato plants derived from hybrid tomato RED CORAL and to the tomato plants derived by the use of methods described herein.

In some embodiments, such methods for producing a tomato plant derived from hybrid tomato RED CORAL comprise (a) self-pollinating the hybrid tomato RED CORAL plant at least once to produce a progeny plant derived from the hybrid tomato RED CORAL. In some embodiments, the methods further comprise (b) crossing the progeny plant derived from the hybrid tomato RED CORAL with itself or a second tomato plant to produce a seed of a progeny plant of a subsequent generation. In some embodiments, the methods further comprise (c) growing the progeny plant of the subsequent generation. In some embodiments, the methods further comprise (d) crossing the progeny plant of the subsequent generation with itself or a second tomato plant to produce a tomato plant further derived from the hybrid tomato RED CORAL. In further embodiments, steps (b), step (c) and/or step (d) are repeated for at least 1, 2, 3, 4, 5, 6, 7, 8, or more generations to produce a tomato plant derived from the hybrid tomato RED CORAL. In some embodiments, within each crossing cycle, the second plant is the same plant as the second plant in the last crossing cycle. In some embodiments, within each crossing cycle, the second plant is different from the second plant in the last crossing cycle.

In some embodiments, provided herewith is a method of producing a tomato plant obtained from hybrid tomato designated RED CORAL, comprising: (a) self-pollinating the tomato plant of the present disclosure at least once to produce a progeny tomato plant obtained from hybrid tomato designated RED CORAL. The method further comprises the steps of: (b) crossing the progeny tomato plant obtained from the hybrid tomato designated RED CORAL with itself or a second tomato plant to produce a progeny seed of a subsequent generation; (c) growing a progeny plant from the progeny seed of the subsequent generation; (d) crossing the progeny plant of the subsequent generation with itself or a second tomato plant to produce a tomato plant derived from the hybrid tomato designated RED CORAL; and (e) repeating step (c) and (d) for at least one generation to produce a tomato plant further derived from the hybrid tomato designated RED CORAL.

Another method for producing a tomato plant derived from hybrid tomato RED CORAL, comprises (a) crossing the hybrid tomato RED CORAL plant with a second tomato plant to produce a progeny plant derived from the hybrid tomato RED CORAL. In some embodiments, the method further comprises (b) crossing the progeny plant derived from the hybrid tomato RED CORAL with itself or a second tomato plant to produce a seed of a progeny plant of a subsequent generation. In some embodiments, the method further comprises (c) growing the progeny plant of the subsequent generation. In some embodiments, the method further comprises (d) crossing the progeny plant of the subsequent generation with itself or a second tomato plant to produce a tomato plant derived from the hybrid tomato RED CORAL. In a further embodiment, steps (b), (c) and/or (d) are repeated for at least 1, 2, 3, 4, 5, 6, 7, 8, or more generations to produce a tomato plant derived from the hybrid tomato RED CORAL. In some embodiments, within each crossing cycle, the second plant is the same plant as the second plant in the last crossing cycle. In some embodiments, within each crossing cycle, the second plant is different from the second plant in the last crossing cycle.

In some embodiments, provided herewith is a method of producing a tomato plant obtained from hybrid tomato designated RED CORAL, comprising: (a) crossing the tomato plant of the present disclosure with a second tomato plant to produce a progeny tomato plant obtained from hybrid tomato designated RED CORAL. The method further comprises the steps of: (b) crossing the progeny tomato plant obtained from the hybrid tomato plant designated RED CORAL with itself or a second tomato plant to produce a progeny seed of a subsequent generation; (c) growing a progeny plant from the progeny seed of the subsequent generation; (d) crossing the progeny plant of the subsequent generation with itself or a second tomato plant to produce a tomato plant derived from the tomato hybrid tomato plant designated RED CORAL; and (e) repeating step (c) and (d) for at least one generation to produce a tomato plant further derived from the hybrid tomato plant designated RED CORAL.

In one aspect, the present disclosure provides methods of introducing a single locus conversion conferring one or more desired trait(s) into the hybrid tomato RED CORAL, and plants, fruits and/or seeds obtained from such methods. In another aspect, the present disclosure provides methods of modifying a single locus and conferring one or more desired trait(s) into the hybrid tomato RED CORAL, and plants, fruits and/or seeds obtained from such methods. The desired trait(s) may be, but not exclusively, conferred by a single locus that contains a single and/or multiple gene(s). In some embodiments, the gene is a dominant allele. In some embodiments, the gene is a partially dominant allele. In some embodiments, the gene is a recessive allele. In some embodiments, the gene or genes will confer or modify such traits, including but not limited to male sterility, herbicide resistance, insect resistance, resistance for bacterial, fungal, *mycoplasma* or viral disease, enhanced plant quality such as improved drought or salt tolerance, water-stress tolerance, improved standability, enhanced plant vigor, improved shelf life, delayed senescence or controlled ripening, enhanced nutritional quality such as increased sugar content or increased sweetness, increased texture, improved flavor and aroma, improved fruit length and/or size, protection for color, fruit shape, uniformity, length or diameter, refinement or depth, lodging resistance, improved yield and recovery, improved fresh cut application, specific aromatic compounds, specific volatiles, flesh texture and specific nutritional components. For the present disclosure and the skilled artisan, disease is understood to include, but not limited to fungal diseases, viral diseases, bacterial diseases, *mycoplasma* diseases, or other plant pathogenic diseases and a disease resistant plant will encompass a plant resistant to fungal, viral, bacterial, *mycoplasma*, and other plant pathogens. In one aspect, the gene or genes may be naturally occurring tomato gene(s) and/or spontaneous or induced mutations(s). In another aspect, genes are mutated, modified, genetically engineered through the use of New Breeding Techniques described herein. In some embodiments, the method for introducing the desired trait(s) into hybrid tomato RED CORAL is a backcrossing process by making use of a series of backcrosses to at least one of the parent lines of hybrid tomato designated RED CORAL (a.k.a. hybrid tomato RED CORAL or tomato hybrid RED CORAL) during which the desired trait(s) is maintained by selection. At least one of the parent lines of hybrid tomato designated RED CORAL possesses the desired trait(s) by the backcrossing process, and the desired trait(s) is inherited by the hybrid tomato progeny plants by conventional breeding techniques known to breeders of ordinary skill in the art. The single gene converted plants or single locus converted plants that can be obtained by the methods are included in the present disclosure.

When dealing with a gene that has been modified, for example through New Breeding Techniques, the trait (genetic modification) could be directly modified into the newly developed hybrid tomato plant and/or at least one of the parent lines of hybrid tomato RED CORAL. Alternatively, if the trait is not modified into each newly developed hybrid tomato plant and/or at least one of the parent lines of hybrid tomato RED CORAL, another typical method used by breeders of ordinary skill in the art to incorporate the modified gene is to take a line already carrying the modified gene and to use such line as a donor line to transfer the modified gene into the newly developed hybrid tomato plant and/or at least one of the parent lines of the newly developed hybrid. The same would apply for a naturally occurring trait or one arising from spontaneous or induced mutations.

In some embodiments, the backcross breeding process of the parental inbred line plants of hybrid tomato RED CORAL comprises (a) crossing one of the parental inbred line plants of hybrid tomato RED CORAL with plants of another line that comprise the desired trait(s) to produce $F_1$ progeny plants. In some embodiments, the process further comprises (b) selecting the $F_1$ progeny plants that have the desired trait(s). In some embodiments, the process further comprises (c) crossing the selected $F_1$ progeny plants with the parental inbred tomato lines of hybrid tomato RED CORAL plants to produce backcross progeny plants. In some embodiments, the process further comprises (d) selecting for backcross progeny plants that have the desired trait(s) and essentially all of the physiological and morphological characteristics of the tomato parental inbred line of hybrid tomato RED CORAL to produce selected backcross progeny plants. In some embodiments, the process further comprises (e) repeating steps (c) and (d) one, two, three, four, five six, seven, eight, nine or more times in succession to produce selected, second, third, fourth, fifth, sixth, seventh, eighth, ninth or higher backcross progeny plants that have the desired trait(s) and essentially all of the characteristics of the parental inbred tomato line of hybrid tomato RED CORAL, and/or have the desired trait(s) and essentially all of the physiological and morphological characteristics of the parental inbred line of hybrid tomato RED CORAL, and/or have the desired trait(s) and otherwise essentially all of the physiological and morphological characteristics of the parental inbred tomato line of tomato hybrid RED CORAL, including but not limited to when grown in the same environmental conditions or including but not limited to at a 5% significance level when grown in the same environmental conditions. In some embodiments, this method further comprises crossing the backcross progeny plant of the parental tomato inbred line plant of hybrid tomato RED CORAL having the desired trait(s) with the second parental inbred tomato line plants of hybrid tomato RED CORAL in order to produce the hybrid tomato RED CORAL comprising the desired trait(s). The tomato plants or seed produced by the methods are also part of the disclosure, as are the hybrid tomato RED CORAL plants that comprise the desired trait. Backcrossing breeding methods, well known to one skilled in the art of plant breeding will be further developed in subsequent parts of the specification.

An embodiment of this disclosure is a method of making a backcross conversion of hybrid tomato RED CORAL. In some embodiments, the method comprises crossing one of the parental tomato inbred line plants of hybrid tomato RED CORAL with a donor plant comprising a spontaneous or artificially induced mutation(s), a naturally occurring gene (s), or a gene(s) and/or sequence(s) modified through New Breeding Techniques conferring one or more desired traits to produce $F_1$ progeny plants. In some embodiments, the method further comprises selecting an $F_1$ progeny plant comprising the naturally occurring gene(s), the spontaneous or artificially induced mutation(s), or the gene(s) and/or sequences(s) modified through New Breeding Techniques conferring the one or more desired traits. In some embodiments, the method further comprises backcrossing the selected progeny plant to the parental tomato inbred line plants of hybrid tomato RED CORAL. This method may further comprise the step of obtaining a molecular marker profile of the parental tomato inbred line plants of hybrid tomato RED CORAL and using the molecular marker profile to select for the progeny plant with the desired trait and the molecular marker profile of the parental tomato inbred line plants of hybrid tomato RED CORAL. In some embodiments, this method further comprises crossing the backcross progeny plant of the parental tomato inbred line plant of hybrid tomato RED CORAL containing the naturally occurring gene(s), the spontaneous or artificially induced mutation(s), or the gene(s) and/or sequence(s) modified through New Breeding Techniques conferring the one or more desired traits, with the second parental inbred tomato line plants of hybrid tomato RED CORAL in order to produce the hybrid tomato RED CORAL comprising the naturally occurring gene(s), the spontaneous or artificially induced mutation(s), or the gene(s) and/or sequence(s) modified through New Breeding Techniques conferring the one or more desired traits. The plants or parts thereof produced by such methods are also part of the present disclosure.

In some embodiments of the disclosure, the number of loci that may be transferred and/or backcrossed into the parental tomato inbred line of hybrid tomato RED CORAL is at least 1, 2, 3, 4, 5, or more.

A single locus may contain several genes. A single locus conversion also allows for making one or more site specific changes to the plant genome, such as, without limitation, one or more nucleotide changes, deletions, insertions, substitutions, etc. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALENs), the CRISPR/Cas endonucleases (using such as Cas9, Cas12a/Cpf1, Cas13/C2c2, CasX and CasY), RNA-guided nucleases, meganucleases, homing endonucleases and endonucleases for DNA guided genome editing (Gao et al., Nature Biotechnology (2016), doi: 10.1038/nbt.3547). In some embodiments, the single locus conversion changes one or several nucleotides of the plant genome. Such genome editing techniques are some of the techniques now known by the person skilled in the art and herein are collectively referred to as "New Breeding Techniques". In some embodiments, one or more above-mentioned genome editing methods are directly applied on a plant of the present disclosure, rather than on the parental tomato inbred lines of hybrid tomato RED CORAL. Accordingly, a cell containing an edited genome, or a plant part containing such cell can be isolated and used to regenerate a novel plant which has a new trait conferred by said genome editing, and essentially all of the physiological and morphological characteristics of hybrid tomato plant RED CORAL.

The disclosure further provides methods for developing tomato plants in a tomato plant breeding program using plant breeding techniques including but not limited to, recurrent selection, backcrossing, pedigree breeding, genomic selection, molecular marker (Isozyme Electrophoresis, Restriction Fragment Length Polymorphisms (RFLPs), Randomly Amplified Polymorphic DNAs (RAPDs), Arbitrarily Primed Polymerase Chain Reactions (AP-PCRs), DNA Amplification Fingerprintings (DAFs), Sequence Characterized Amplified Regions (SCARs), Amplified Fragment Length Polymorphisms (AFLPs), and Simple Sequence Repeats (SSRs) which are also referred to as Microsatellites, Single Nucleotide Polymorphisms (SNPs), enhanced selection, genetic markers, enhanced selection and transformation. Seeds, tomato plants, and parts thereof produced by such breeding methods are also part of the disclosure.

The disclosure also relates to variants, mutants and trivial modifications of the seed or plant of the hybrid tomato RED CORAL or inbred parental lines thereof. Variants, mutants and trivial modifications of the seed or plant of hybrid tomato RED CORAL or inbred parental lines thereof can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knockouts/knock-ins, antisense oligonucleotides, RNA interference and other techniques such as the New Breeding Techniques described herein. For more information of mutagenesis in plants, such as agents or protocols, see Acquaah et al. (Principles of plant genetics and breeding, Wiley-Blackwell, 2007, ISBN 1405136464, 9781405136464, which is herein incorporated by reference in its entity).

The disclosure also relates to a mutagenized population of the hybrid tomato RED CORAL and methods of using such populations. In some embodiments, the mutagenized population can be used in screening for new tomato plants which comprise essentially one or more of or all the morphological and physiological characteristics of hybrid tomato RED CORAL. In some embodiments, the new tomato plants obtained from the screening process comprise essentially all of the morphological and physiological characteristics of the hybrid tomato RED CORAL, and one or more additional or different morphological and physiological characteristics that the hybrid tomato RED CORAL does not have.

This disclosure is also directed to methods for producing a tomato plant by crossing a first parent tomato plant with a second parent tomato plant, wherein either the first or second parent tomato plant is a hybrid tomato plant of RED CORAL. Further, both first and second parent tomato plants can come from the hybrid tomato plant RED CORAL. Further, the hybrid tomato plant RED CORAL can be self-pollinated i.e. the pollen of a hybrid tomato plant RED CORAL can pollinate the ovule of the same hybrid tomato plant RED CORAL. When crossed with another tomato plant, a hybrid seed is produced. Such methods of hybridization and self-pollination are well known to those skilled in the art of breeding.

An inbred tomato line such as one of the parental lines of hybrid tomato RED CORAL has been produced through several cycles of self-pollination and is therefore to be considered as a homozygous line. An inbred line can also be produced though the dihaploid system which involves doubling the chromosomes from a haploid plant or embryo thus resulting in an inbred line that is genetically stable (homozygous) and can be reproduced without altering the inbred line. Haploid plants could be obtained from haploid embryos that might be produced from microspores, pollen, anther cultures or ovary cultures or spontaneous haploidy. The haploid embryos may then be doubled by chemical treatments such as by colchicine or be doubled autonomously. The haploid embryos may also be grown into haploid plants and treated to induce the chromosome doubling. In either case, fertile homozygous plants may be obtained. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting $F_1$ hybrid, theoretically in the arrangement and organization created by the plant breeder in the original parental line.

As long as the homozygosity of the parental lines is maintained, the resulting hybrid cross shall be stable. The F1 hybrid is then a combination of phenotypic characteristics issued from two arrangement and organization of genes, both created by a person skilled in the art through the breeding process.

Still further, this disclosure is also directed to methods for producing a tomato plant derived from hybrid tomato RED CORAL by crossing hybrid tomato plant RED CORAL with a second tomato plant. In some embodiments, the methods further comprise obtaining a progeny seed from the cross. In some embodiments, the methods further comprise growing the progeny seed, and possibly repeating the crossing and growing steps with the hybrid tomato plant RED CORAL derived plant from 0 to 7 or more times. Thus, any such methods using the hybrid tomato plant RED CORAL are part of this disclosure: selfing, backcrosses, hybrid production, crosses to populations, and the like. All plants produced using hybrid tomato plant RED CORAL as a parent are within the scope of this disclosure, including plants derived from hybrid tomato plant RED CORAL. In some embodiments, such plants have one, more than one or all of the physiological and morphological characteristics of the hybrid tomato plant RED CORAL including but not limited to as determined at the 5% significance level when grown in the same environmental conditions. In some embodiments, such plants might exhibit additional and desired characteristics or traits such as high seed yield, high seed germination, seedling vigor, early maturity, high fruit yield, ease of fruit setting, disease tolerance or resistance, lodging resistance, and adaptability for soil and climate conditions. Consumer-driven traits, such as a preference for a given fruit size, fruit shape, fruit color, fruit texture, fruit taste, fruit firmness, fruit sugar content are other traits that may be incorporated into new tomato plants developed by this disclosure.

A tomato plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots, or is grafted onto a tomato plant or a rootstock prepared to support growth of shoot tissue. This is achieved using methods well known in the art. Accordingly, in one embodiment, a method of vegetatively propagating a plant of the present disclosure comprises collecting a part of a plant according to the present disclosure, e.g. a shoot tissue, and obtaining a plantlet from said part. In one embodiment, a method of vegetatively propagating a plant of the present disclosure comprises: (a) collecting tissue of a plant of the present disclosure; (b) rooting said proliferated shoots to obtain rooted plantlets. In one embodiment, a method of vegetatively propagating a plant of the present disclosure comprises: (a) collecting tissue of a plant of the present disclosure; (b) cultivating said tissue to obtain proliferated shoots; (c) rooting said proliferated shoots to obtain rooted plantlets. In one embodiment, such method further comprises growing a plant from said plantlets. In one embodiment, a fruit is harvested from said plant. In one embodiment, such fruits and plants have all of the physiological and morphological characteristics of fruits and plants of hybrid tomato designated RED CORAL when grown in the same environmental conditions. In one embodiment, the fruit is processed into products such as canned tomato fruits and/or parts thereof, freeze dried or frozen fruit and/or parts thereof, fresh or prepared fruit and/or parts thereof or pastes, sauces, purees, catsups and the like.

The disclosure is also directed to the use of the hybrid tomato plant RED CORAL in a grafting process. In one embodiment, the hybrid tomato plant RED CORAL is used as the scion while in another embodiment, the hybrid tomato plant RED CORAL is used as a rootstock.

In some embodiments, the present disclosure teaches a seed of hybrid tomato designated RED CORAL, wherein a representative sample of seed of said hybrid is deposited under NCIMB No. 44216.

In some embodiments, the present disclosure teaches a tomato plant, or a part thereof, produced by growing the deposited RED CORAL seed.

In some embodiments, the present disclosure teaches a tomato plant part, wherein the tomato part is selected from the group consisting of: a leaf, a flower, a fruit, a stalk, a root, a rootstock, a seed, an embryo, a peduncle, a stamen, an anther, a pistil, an ovule, a pollen, a cell, a rootstock, and a scion.

In some embodiments, the present disclosure teaches a tomato plant, or a part thereof, having all of the characteristics of hybrid tomato RED CORAL deposited under NCIMB No. 44216 of this disclosure including but not limited to as determined at the 5% significance level when grown in the same environmental conditions.

In some embodiments, the present disclosure teaches a tomato plant, or a part thereof, having all of the physiological and morphological characteristics of hybrid tomato RED CORAL, wherein a representative sample of seed of said hybrid was deposited under NCIMB No. 44216.

In some embodiments, the present disclosure teaches a tissue culture of regenerable cells produced from the plant or part grown from the deposited RED CORAL seed, wherein cells of the tissue culture are produced from a plant part selected from the group consisting of protoplasts, embryos, meristematic cells, callus, pollens, ovules, flowers, seeds, leaves, roots, root tips, anthers, stems, petioles, fruits, axillary buds, cotyledons and hypocotyls. In some embodiments, the plant part includes protoplasts produced from a plant grown from the deposited RED CORAL seed.

In some embodiments, the present disclosure teaches a composition comprising regenerable cells produced from the plant or part thereof grown from the deposited hybrid RED CORAL seed, or other part or cell thereof. In some embodiments, the composition further comprises a growth media. In some embodiments, the growth media is solid or a synthetic cultivation medium. In some embodiments, the composition is a tomato plant regenerated from the tissue culture from a plant grown from the deposited RED CORAL seed, said plant having all of the characteristics of hybrid tomato RED CORAL, wherein a representative sample of seed of said hybrid is deposited under NCIMB No. 44216.

In some embodiments, the present disclosure teaches a tomato fruit produced from the plant grown from the deposited RED CORAL seed.

In some embodiments, such fruits have all of the physiological and morphological characteristics of hybrid tomato designated RED CORAL fruits when grown in the same environmental conditions.

In some embodiments, methods of producing said tomato fruit comprise (a) growing the tomato plant from deposited RED CORAL seed to produce a tomato fruit, and (b) harvesting said tomato fruit. In some embodiments, the present disclosure also teaches a tomato fruit produced by the method of producing tomato fruit and/or seed as described above. In some embodiments, such fruits have all of the physiological and morphological characteristics of fruits of hybrid tomato designated RED CORAL (e.g. those listed in Table 1 and/or deposited under NCIMB No. 44216) when grown in the same environmental conditions.

In some embodiments, the present disclosure teaches methods for producing a tomato seed comprising crossing a first parent tomato plant with a second parent tomato plant and harvesting the resultant tomato seed, wherein said first parent tomato plant and/or second parent tomato plant is the tomato plant produced from the deposited RED CORAL seed or a tomato plant having all of the characteristics of hybrid tomato RED CORAL deposited under NCIMB No. 44216 including but not limited to as determined at the 5% significance level when grown in the same environmental conditions.

In some embodiments, the present disclosure teaches methods for producing a tomato seed comprising self-pollinating the tomato plant grown from the deposited RED CORAL seed and harvesting the resultant tomato seed.

In some embodiments, the present disclosure teaches the seed produced by any of the above described methods.

In some embodiments, the present disclosure teaches methods of vegetatively propagating the tomato plant grown from the deposited RED CORAL seed, said method comprising collecting a part of a plant grown from the deposited RED CORAL seed and regenerating a plant from said part.

In some embodiments, the method further comprises harvesting fruits and/or seeds from said vegetatively propagated plant. In some embodiments, the method further comprises harvesting a fruit from said vegetatively propagated plant.

In some embodiments, the present disclosure teaches the plant and the fruits and/or seeds of plants vegetatively propagated from parts of plants grown from the deposited RED CORAL seed. In some embodiments, such plant, fruits and/or seeds have all of the physiological and morphological characteristics of plant, fruits and/or seeds of hybrid tomato RED CORAL (e.g. those listed in Table 1 and/or deposited under NCIMB No. 44216) when grown in the same environmental conditions.

In some embodiments, the present disclosure teaches methods of producing a tomato plant derived from the hybrid tomato RED CORAL. In some embodiment, the methods comprise (a) self-pollinating the plant grown from the deposited RED CORAL seed at least once to produce a progeny plant derived from tomato hybrid RED CORAL. In some embodiments, the method further comprises (b) crossing the progeny plant derived from tomato hybrid RED CORAL with itself or a second tomato plant to produce a seed of a progeny plant of a subsequent generation; and; (c) growing the progeny plant of the subsequent generation from the seed, and (d) crossing the progeny plant of the subsequent generation with itself or a second tomato plant to produce a tomato plant derived from the hybrid tomato variety RED CORAL. In some embodiments said methods further comprise the step of: (e) repeating steps (b), (c) and/or (d) for at least 1, 2, 3, 4, 5, 6, 7, or more generation to produce a tomato plant derived from the hybrid tomato variety RED CORAL.

In some embodiments, the present disclosure teaches methods of producing a tomato plant derived from the hybrid tomato RED CORAL, the methods comprising (a) crossing the plant grown from the deposited RED CORAL seed with a second tomato plant to produce a progeny plant derived from hybrid tomato RED CORAL. In some embodiments, the method further comprises; (b) crossing the progeny plant derived from hybrid tomato RED CORAL with itself or a second tomato plant to produce a seed of a progeny plant of a subsequent generation; and; (c) growing the progeny plant of the subsequent generation from the seed; (d) crossing the progeny plant of the subsequent generation with itself or a second tomato plant to produce a tomato plant derived from the hybrid tomato variety RED CORAL. In some embodiments said methods further comprise the steps of: (e) repeating steps (b), (c) and/or (d) for at least 1, 2, 3, 4, 5, 6, 7 or more generations to produce a tomato plant derived from the hybrid tomato variety RED CORAL.

In some embodiments, the present disclosure teaches plants grown from the deposited RED CORAL seed wherein said plants comprise a single locus conversion. As used herein, the term "a" or "an" refers to one or more of that entity; for example, "a single locus conversion" refers to one or more single locus conversions or at least one single locus conversion. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

In some embodiments, the present disclosure teaches a method of producing a plant of hybrid tomato designated RED CORAL comprising at least one desired trait, the method comprising introducing a single locus conversion conferring the desired trait into hybrid tomato designated RED CORAL, whereby a plant of hybrid tomato designated RED CORAL comprising the desired trait is produced.

In some embodiments, the present disclosure teaches a tomato plant, comprising a single locus conversion and otherwise all of the characteristics of hybrid tomato designated RED CORAL when grown under the same environmental conditions, wherein a representative sample of seed of said hybrid has been deposited under NCIMB No. 44216. In some embodiments, the single locus conversion is an artificially mutated gene or nucleotide sequence. In other embodiments, the single locus conversion is introduced into the plant by the use of recurrent selection, mutation breeding, wherein said mutation breeding selects for a mutation that is spontaneous or artificially induced, backcrossing, pedigree breeding, haploid/double haploid production, marker-assisted selection, genetic transformation, genomic selection, oligonucleotide directed mutagenesis, cisgenesis, intragenesis, RNA-dependent DNA methylation, agro-infiltration, Zinc finger nuclease (ZFN), Transcription Activation-Like Effector Nuclease (TALENs), CRISPR/Cas system, engineered meganuclease, engineered homing endonuclease, and DNA guided genome editing. In further embodiments, the single locus conversion is introduced into the plant by a gene/genome editing technique with a nuclease selected from the group consisting of Zinc finger nuclease (ZFN), Transcription Activation-Like Effector Nuclease (TALEN), Clustered Regularly Interspaced Short Palindromic Repeats-associated Cas endonuclease (CRISPR-Cas), meganuclease, homing endonuclease, and RNA-guided nuclease.

A further embodiment relates to a method for developing a tomato plant in a tomato plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the tomato plant of 'RED CORAL', or its parts, wherein application of said techniques results in development of a tomato plant.

A further embodiment relates to a method of introducing a mutation into the genome of tomato plant 'RED CORAL', said method comprising mutagenesis of the plant, or plant part thereof, of 'RED CORAL', wherein said mutagenesis is selected from the group consisting of temperature, long-term seed storage, tissue culture conditions, ionizing radiation, chemical mutagens, and targeting induced local lesions in genomes, and wherein the resulting plant comprises at least one genome mutation and producing plants therefrom.

A further embodiment relates to a method of editing the genome of tomato plant 'RED CORAL', wherein said method is a gene/genome editing technique with a nuclease selected from the group consisting of Zinc finger nuclease (ZFN), Transcription Activation-Like Effector Nuclease (TALEN), Clustered Regularly Interspaced Short Palindromic Repeats-associated Cas endonuclease (CRISPR-Cas), meganuclease, homing endonuclease, and RNA-guided nuclease, and plants produced therefrom.

In some embodiments, the plant comprises 1, 2, 3, 4, 5, 6, 7, 8, 9, 10, or more single locus conversions. In some embodiments, the plant comprises no more than 1, 2, 3, 4, 5, 6, 7, 8, 9, or 10 single locus conversions, but essentially all of the other physiological and morphological characteristics of hybrid tomato plant RED CORAL deposited under NCIMB No. 44216. In some embodiments, the plant comprises at least one single locus conversion and essentially all of the physiological and morphological characteristics of hybrid tomato plant RED CORAL deposited under NCIMB No. 44216. In other embodiments, the plant comprises one single locus conversion and essentially all of the other physiological and morphological characteristics of hybrid tomato plant RED CORAL deposited under NCIMB No. 44216.

In some embodiments, said single locus conversion confers said plants with a trait selected from the group consisting of male sterility, male fertility, herbicide resistance, insect resistance, resistance for bacterial, fungal, *mycoplasma* or viral disease, enhanced plant quality such as improved drought or salt tolerance, water stress tolerance, improved standability, enhanced plant vigor, improved shelf life, delayed senescence or controlled ripening, increased nutritional quality such as increased sugar content or increased sweetness, increased texture, improved flavor and aroma, improved fruit length and/or size, protection for color, fruit shape, uniformity, length or diameter, refinement or depth lodging resistance, improved yield and recovery when compared to a suitable check/comparison plant. In further embodiments, the single locus conversion confers said plant with herbicide resistance.

In some embodiments, the check plant is a hybrid tomato RED CORAL not having said single locus conversion conferring the desired trait(s). In some embodiments, the at least one single locus conversion is a spontaneous or artificially mutated gene, or a gene and/or nucleotide sequence modified through the use of New Breeding Techniques.

In some embodiments, the present disclosure teaches methods of producing a tomato plant, comprising grafting a rootstock or a scion of the hybrid tomato plant grown from the deposited RED CORAL seed to another tomato plant. In some embodiments, the present disclosure teaches methods for producing nucleic acids, comprising isolating nucleic acids from the plant grown from the deposited RED CORAL seed, or a part, or a cell thereof. In some embodiments, the present disclosure teaches methods for producing a second tomato plant, comprising applying plant breeding techniques to the plant grown from the deposited RED CORAL seed, or part thereof to produce the second tomato plant.

In some embodiments, the present disclosure provides a method of producing a commodity plant product comprising collecting the commodity plant product from the plant of the present disclosure. The commodity plant product produced by said method is also part of the present disclosure.

In addition to the exemplary aspects and embodiments described above, further aspects and embodiments will become apparent by study of the following descriptions.

DETAILED DESCRIPTION OF THE DISCLOSURE

The following description includes information that may be useful in understanding the present disclosure. It is not an admission that any of the information provided herein is prior art or relevant to the present disclosure, or that any publication specifically or implicitly referenced is prior art.

Definitions

In the description and tables that follow, a number of terms are used. In order to provide a clear and consistent understanding of the specification and claims, including the scope to be given such terms, the following definitions are provided:

Abscission zone: This is the zone of abscission or area of separation of the leaves, flowers, and fruits from the plant. For flower abscission, the resulting zone (or blossom scar) ranges in size, small being preferred over large-range small (<10 mm), medium (10-15 mm), large (15-20 mm), very large (>20 mm).

Adaptability: A plant that has adaptability is a plant able to grow well in different growing conditions (climate, soils, etc.).

Allele: An allele is a variant form of a gene or locus.

Androecious plant: A plant having staminate flowers only.

Backcrossing: Backcrossing is a process in which a breeder repeatedly crosses hybrid progeny back to one of the parents, for example, a first-generation hybrid $F_1$ with one of the parental genotypes of the $F_1$ hybrid.

Blotchy: Abnormal coloration characterized by the presence of green areas on the surface of red ripe fruit and sub-surface brown areas associated with the sub-epidermal cell layers. Variations in light, water and temperature as well as nutritional disorders can cause irregular maturity and blotchy color.

Blossom scar: This is the remnant scar from the stigmatic surface of the blossom. There is a very broad range in sizes, small is better. Range is small (<10 mm), medium (10-20 mm), large (20-40 mm) and very large (>40 mm).

Cavity: As used herein, cavity refers to the center of the tomato fruit containing seeds and maternal tissues. Cavity measurements are made on a single fruit or recorded as an average of many fruit at harvest maturity and recorded in a convenient unit of measure.

Cavity ratings: 1=very poor (non-marketable), 3=poor (non-marketable), 5=average (marketable) 7=very good (much better than industry standards), 9=superior (further improvement not attainable). Cavity evaluations are done based on a combination of the cavity size and the degree of open space in the cavity. Very poor would be open and very large; superior would be very small and closed.

Cavity to Diameter ratio: Cavity to Diameter ratio is a measure of the cavity size compared to the overall fruit size of a single fruit or the average of many fruit at harvest maturity and recorded in a convenient unit of measure.

Commodity plant product: A "commodity plant product" refers to any composition or product that is comprised of material derived from a plant, seed, plant cell, or plant part of the present disclosure. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; biomasses and fuel products; and raw material in industry.

Collection of seeds: In the context of the present disclosure a collection of seeds is a grouping of seeds mainly containing similar kind of seeds, for example hybrid seeds of the disclosure, but that may also contain, mixed together with this first kind of seeds, a second, different kind of seeds, of one of the inbred parent lines, for example the inbred line of the present disclosure. A commercial bag of hybrid seeds of the disclosure and containing also the inbred parental line seeds would be, for example such a collection of seeds.

Cracking: a physiological disorder characterized by the appearance of rough corky surface cracks in the tomato fruit caused by sub-surface cuticle cells bursting and russeting. Cracking is a commercial defect that generally makes the fruit unmarketable.

Determinate tomatoes: Determinate tomatoes are tomato varieties that come to fruit all at once, then stop bearing. They are best suited for commercial growing and mechanical harvesting since they can be harvested all at once.

Decreased vigor: A plant having a decreased vigor in the present disclosure is a plant that, compared to other plants has a less vigorous appearance for vegetative and/or reproductive characteristics including but not limited to shorter plant height, smaller fruit size, fewer fruit or other characteristics.

Earliness: The earliness relates the number of fruits produced from 12 to 15 days following the beginning of the harvest: the more fruits produced, the more earliness of the plant Easy to pick fruit: A fruit that is easy to pick is a fruit that easily detaches from the plant. Once grabbed and twisted, the fruit will break between the peduncle and the stem. For fruits not easy to pick, the peduncle breaks off the fruits. A fruit that is easy to pick is also a fruit that is easily accessible for harvest. When plants have an open plant habit, the fruits are harvested more easily than when the plants have closed habit.

Enhanced nutritional quality: The nutritional quality of the tomato of the present disclosure can be enhanced by the introduction of several traits comprising a higher endosperm sugar content, flesh texture, brix, aroma content and increased sweetness, increased lycopene content of the peel, etc.

Essentially all of the physiological and morphological characteristics: A plant having essentially all of the physiological and morphological characteristics means a plant having all of the physiological and morphological characteristics of a plant of the present disclosure, except for additional traits and/or mutations which do not materially affect the plant of the present disclosure, or a desired characteristic(s), which can be indirectly obtained from another plant possessing at least one single locus conversion via a conventional breeding program (such as backcross breeding) or directly obtained by introduction of at least one single locus conversion via New Breeding Techniques. In some embodiments, one of the non-limiting examples for a plant having (and/or comprising) essentially all of the physiological and morphological characteristics shall be a plant having all of the physiological and morphological characteristics of a plant of the present disclosure other than desired, additional trait(s)/characteristic(s) conferred by a single locus conversion including, but not limited to, a converted or modified gene.

Extended harvest: An extended harvest is a plant that produces fruits throughout the harvest season.

Flesh color: In the context of the present disclosure, the flesh color is the color of the tomato flesh.

Field holding ability: Field holding ability is the ability for fruit quality to maintain even after fruit is ripe.

Firm Fruit Exterior: Fruit Firmness subjectively tested under field conditions for resistance of fruit exterior against a given pressure. Range is soft, medium, firm and very firm and hard shell.

Grafting: Grafting is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

Good Seed Producer: A plant is a good seed producer when it produces numerous seeds. For tomato, a good seed producing plant will produce an average of 20 grams of seeds during the harvest season.

Gynoecious plant: A plant having pistillate flowers only.

Immunity to disease(s) and or insect(s): A tomato plant which is not subject to attack or infection by specific disease(s) and or insect(s) is considered immune.

Industrial usage: The industrial usage of the tomato of the present disclosure comprises the use of the tomato fruit for consumption, whether as fresh products or in canning, freezing or any other industries.

Intermediate resistance to disease(s), pest(s) and/or insect(s): A tomato plant that restricts the growth and development of specific disease(s), pest(s) and/or insect(s), but may exhibit a greater range of symptoms or damage compared to a resistant plant. Intermediate resistant plants will usually show less severe symptoms or damage than susceptible plant varieties when grown under similar environmental conditions and/or specific disease(s), pest(s) and/or insect(s) pressure, but may have heavy damage under heavy pressure. Intermediate resistant tomato plants are not immune to the disease(s), pest(s) and/or insect(s).

Monecious: The term used to describe a plant variety where each flower exhibits only one sexual character (either male or female) and each plant has flowers of both sexes.

Maturity: In the region of best adaptability, maturity is the number of days from transplanting to optimal time for fruit harvest.

New Breeding Techniques: New breeding techniques (NBTs) are said of various new technologies developed and/or used to create new characteristics in plants through genetic variation, the aim being targeted mutagenesis, targeted introduction of new genes or gene silencing. The following breeding techniques are within the scope of NBTs: targeted sequence changes facilitated through the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), genome editing with endonucleases such as chemical nucleases, engineered meganucleases, engineered homing endonucleases, ZFNs, Transcription Activator-Like Effector Nucleases (TALENs, see U.S. Pat. Nos. 8,586,363 and 9,181,535, incorporated by reference in their entireties), the CRISPR/Cas system including RNA-guided endonucleases (using such as Cas9, Cas12a/Cpf1, Cas13/C2c2, CasX and CasY; also see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques-State-of-the-art and prospects for commercial development", which is incorporated by reference in its entirety.

Number of Boxes per Acre: The Number of Boxes per Acre-6's, 9's, 12's, 15's, 18's or 23's refers to the number of fruit that fit into a standard tomato box.

Open Plant Habit: An open plant habit is a plant where the fruits are visible without moving the leaves. A plant with closed habit will have its fruit hidden by leaves that have a high density. An average open plant habit will be between the open and closed habit, and the plant will have medium leaf density. Whether a plant has open habit or closed habit is based on the whole of the plant. The more erect the plant, the more compact and therefore the closer the habit. In contrast, when the plant is lodging, sprawling on the ground, it leads to a less compact plant, therefore more "open".

Overall Rating: A final or Overall Rating is assigned to variety performance or a varieties characteristic in test or trial situations of a variety. Overall Rating can range from 1=very poor to 10 excellent.

Oval: Oval is used to describe fruit shape when the length is greater than the width and ranges from a slight oval, oval to heavy oval.

Plant adaptability: A plant having good plant adaptability means a plant that will perform well in different growing conditions and seasons.

Plant cell: As used herein, the term "plant cell" includes plant cells whether isolated, in tissue culture, or incorporated in a plant or plant part.

Plant height: Plant height is taken from the top of the soil to the top of the plant leaf canopy and is measured in centimeters or inches.

Plant Part: As used herein, the term "plant part", "part thereof" or "parts thereof" includes plant cells, plant protoplasts, plant cell tissue cultures from which tomato plants can be regenerated, plant calli, plant clumps and plant cells that are intact in plants or parts of plants, such as embryos, pollens, ovules, flowers, seeds, fruits, rootstocks, scions, stems, roots, anthers, pistils, root tips, leaves, meristematic cells, axillary buds, hypocotyls, cotyledons, ovaries, seed coats, endosperms and the like. In some embodiments, the plant part at least comprises at least one cell of said plant. In some embodiments, the plant part is further defined as a pollen, a meristem, a cell or an ovule. In some embodiments, a plant regenerated from the plant part has all of the phenotypic and morphological characteristics of a tomato hybrid of the present disclosure, including but not limited to as determined at the 5% significance level when grown in the same environmental conditions.

Plant Habit: A plant can be an upright plant (also called erect) providing good coverage for the fruit or it can be open with a weaker habit exposing the fruit Predicted paste bostwick. The predicted paste bostwick is the calculated number with the brix and Bostwick reading using the following formula: Predicted paste bostwick=– 11.53+ (1.64*juice brix)+ (0.5*juice bostwick).

Quantitative Trait Loci (QTL): Quantitative trait loci refer to genetic loci that control to some degree numerically representable traits that are usually continuously distributed.

Regeneration: Regeneration refers to the development of a plant from tissue culture.

Resistance to disease(s), pest(s) and/or insect(s): A tomato plant that restricts the growth and development of specific disease(s), pest(s) and/or insect(s) under normal disease(s) and or insect(s) attack pressure when compared to susceptible plants. These tomato plants can exhibit some symptoms or damage under heavy disease(s), pest(s) and/or insect(s) pressure. Resistant tomato plants are not immune to the disease(s), pest(s) and/or insect(s).

Rootstock: A rootstock is the lower part of a plant capable of receiving a scion in a grafting process.

RHS: RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Scion: A scion is the higher part of a plant capable of being grafted onto a rootstock in a grafting process.

Relative maturity or maturity: Maturity is considered the date of the onset of harvest and is classified as Very Early, Early, Mid Early, Intermediate and Late as specified by recording the date of the onset of harvest. In the region of best adaptability, maturity is the number of days from transplanting to optimal time for fruit harvest. In this region, a mid-early maturity plant is a plant that is harvested approximately 80-90 days after transplanting. Very early maturity plant would have less than 70 days from transplanting until harvest, while an early maturity plant would have 70-80 days from transplanting to harvest. An intermediate maturity plant will have 90-100 days from transplanting until harvest, while a late maturity plant will have 100 days until harvest.

Semi-erect habit: A semi-erect plant has a combination of lateral and upright branching and has an intermediate type habit between a prostate plant habit, having laterally growing branching with fruits most of the time on the ground and an erect plant habit with branching going straight up with fruit being off the ground.

Shape: Refers to external fruit shape. Range is Flat Round, Round, round oval, oval, elongate.

Single locus converted (conversion): Single locus converted (conversion) plants refer to plants which are developed by a plant breeding technique called backcrossing, wherein essentially all of the desired morphological and physiological characteristics of a plant are recovered in addition to a single locus transferred into the plant via the backcrossing technique or via genetic engineering. A single locus converted plant can also be referred to a plant with a single locus conversion obtained though simultaneous and/ or artificially induced mutagenesis or through the use of New Breeding Techniques described in the present disclosure. In some embodiments, the single locus converted plant has essentially all of the desired morphological and physiological characteristics of the original variety in addition to a single locus converted by spontaneous and/or artificially induced mutations, which is introduced and/or transferred into the plant by the plant breeding techniques such as backcrossing. In other embodiments, the single locus converted plant has essentially all of the desired morphological and physiological characteristics of the original variety in addition to a single locus, gene or nucleotide sequence(s) converted, mutated, modified or engineered through the New Breeding Techniques taught herein. In the present disclosure, single locus converted (conversion) can be interchangeably referred to single gene converted (conversion).

Soluble Solids: Soluble solids refer to the percent of solid material found in the fruit tissue, the vast majority of which are sugars. Soluble solids are estimated with a refractometer and measured as degrees Brix. Soluble Solids vary with environment. For example, for California summer growing conditions the following range would apply. Very high (>12.5%), high (11.5-12.5%), medium (10.5-11.5%), low<10.5%).

Susceptible to disease(s) and/or insect(s): A tomato plant that is susceptible to disease(s) and/or insect(s) is defined as a tomato plant that has the inability to restrict the growth and development of specific disease(s) and/or insect(s). Plants that are susceptible will show damage when infected and are more likely to have heavy damage under moderate levels of specific disease(s) and/or insect(s).

Tolerance to abiotic stresses: A tomato plant that is tolerant to abiotic stresses has the ability to endure abiotic stress without serious consequences for growth, appearance and yield.

Uniformity: Uniformity, as used herein, describes the similarity between plants or plant characteristics which can be a described by qualitative or quantitative measurements.

Variety: A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants). The term "variety" can be interchangeably used with "cultivar," "line," or "hybrid in the present application.

Yield (Tomato yield Tons/Acre): The yield in tons/acre is the actual yield of the tomato fruit at harvest.

Tomato Plants

Practically speaking, all cultivated forms of tomato belong to a species now known as *Solanum lycopersicum* L. This was the original classification and is now considered correct and the former designation, *Lycopersicon esculentum* Miller, is widely used in older literature, but is no longer considered correct. *Solanum* is a genus within the extremely large and diverse family Solanaceae which is considered to consist of around 90 genera, including pepper, tobacco and eggplant. The genus *Lycopersicon* has been divide into two subgenera, the *esculentum* complex which contains those species that can easily be crossed with the commercial tomato and the *peruvianum* complex which contains those species which are crossed with considerable difficulty (Stevens, M., and Rick, C. M. 1986. Genetics and Breeding. In: The Tomato Crop. A scientific basis for improvement, pp. 35-109. Atherton, J., Rudich, G. (eds.). Chapman and Hall, New York). Due to its value as a crop, *L. esculentum* Miller has become widely disseminated all over the world. Even if the precise origin of the cultivated tomato is still somewhat unclear, it seems to come from the Americas, being native to Ecuador, Peru and the Galapagos Island and initially cultivated by Aztecs and Incas as early as 700 AD. Mexico appears to have been the site of domestication and the source of the earliest introduction.

It is supposed that the cherry tomato, *L. esculentum* var. *cerasiforme*, is the direct ancestor of modern cultivated forms.

Tomato is grown for its fruit, widely used as a fresh market or processed product. As a crop, tomato is grown commercially wherever environmental conditions permit the production of an economically viable yield. In California, the first largest processing tomato market and second largest fresh market in the United States, processing tomato are harvested by machine. The majority of fresh market tomatoes are harvested by hand at vine ripe and mature green stage of ripeness. Fresh market tomatoes are available in the United States year round. Processing tomato season in California is from late June to October. Processing tomato are used in many forms, as canned tomatoes, tomato juice, tomato sauce, puree, paste or even catsup. Over the 500,000 acres of tomatoes that are grown annually in the US, approximately 40% are grown for fresh market consumption, the balance are grown for processing.

Tomato is a normally simple diploid species with twelve pairs of differentiated chromosomes. However, polyploid tomato is also part of the present disclosure. The cultivated tomato is self-fertile and almost exclusively self-pollinating. The tomato flowers are hermaphrodites. Commercial cultivars were initially open pollinated. Most have now been replaced by better yielding hybrids. Due to its wide dissemination and high value, tomato has been intensively bred. This explains why such a wide array of tomato is now available. The shape may range from small to large, and there are cherry, plum, pear, blocky, round, and beefsteak types. Tomatoes may be grouped by the amount of time it takes for the plants to mature fruit for harvest and, in general, the cultivars are considered to be early, midseason or late-maturing. Tomatoes can also be grouped by the plant's growth habit; determinate or indeterminate. Determinate plants tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. More recent developments in tomato breeding have led to a wider array of fruit color. In addition to the standard red ripe color, tomatoes can be creamy white, lime green, pink, yellow, golden, orange or purple.

Hybrid vigor has been documented in tomatoes and hybrids are gaining more and more popularity amongst farmers with uniformity of plant characteristics.

Hybrid commercial tomato seed is produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In tomato, these important traits may include increased fruit number, fruit size and fruit weight, higher seed yield, improved color, resistance to diseases, pests and insects, tolerance to drought and heat, better uniformity, higher nutritional value and better agronomic quality, growth rate, high seed germination, seedling vigor, early fruit maturity, ease of fruit setting, adaptability for soil and climate conditions, firmness, content in soluble solids, acidity and viscosity. With mechanical harvesting of processing tomato, fruit setting concentration, harvestability and field holding are also very important.

In some embodiments, particularly desirable traits that may be incorporated by this disclosure are improved resistance to different viral, fungal, and bacterial pathogens and improved resistance to insect pests. Important diseases include but are not limited to Tomato yellow leaf curl virus, Tomato spot wilt virus, etc. Improved resistance to insect pests is another desirable trait that may be incorporated into new tomato plants developed by this disclosure. Insect pests affecting the various species of tomato include, but not limited to arthropod pests such as *Tuta absoluta, Frankliniella occidentalis, Bemisia tabaci*, etc.

Other desirable traits include traits related to improved tomato fruits. A non-limiting list of fruit phenotypes used during breeding selection include:

Average of juice bostwick: The juice Bostwick a measurement of the viscosity. The viscosity or consistency of tomato products is affected by the degree of concentration of the tomato, the amount of and extent of degradation of pectin, the size, shape and quality of the pulp, and probably to a lesser extent, by the proteins, sugars and other soluble constituents. The viscosity is measured in Bostwick centimeters by using instruments such as a Bostwick Consistometer.

pH: The pH is a measure of acidity of the fruit puree. A pH under 4.5 is desirable to prevent bacterial spoilage of finished products. pH rises as fruit matures.

Fruit color: Fruit color is measured as Hunters a/b ratio, where a represents red/green, positive values are red, negative values are green and 0 is neutral; b represents yellow/blue, where positive values are yellow, negative values are blue and 0 is neutral; a/b represents the intense of redness: large value represents deep red color, small value represents light or yellowish red color.

Fruit Weight: The weight of a single fruit or the average of many fruit measured at harvest maturity and recorded in a convenient unit of measure.

Ostwald: The Ostwald is a measurement of serum viscosity whereas the measurement are taken using an Ostwald viscometer. The serum is the non-solid portion of a tomato extract after centrifugation of the tomato puree. The serum viscosity is affected by the quantity and quality of soluble pectin. Higher number reflect higher viscosity of the tomato serum.

Fruit firmness: The fruit firmness is the resistance to penetration and is measured using a Digital Durometer Model DD-4-00 (Rex Gauge Company, Buffalo Grove, IL, USA). Durometer readings are taken at 4 locations (each about 90 degrees apart) on the approximate mid-point of a tomato, with the tomato laying on its side. From a fruit sample collected at a given location, the resistance to penetration is measured with the durometer from 9 individual fruit at 4 locations per fruit (a total of 36 independent measurements). The P5 value is calculated from the following equation: D-39/10, where D is the value from the Durometer.

Tomato Breeding

The goal of tomato breeding is to develop new, unique and superior tomato inbred lines and hybrids. The breeder initially selects and crosses two or more parental lines, followed by repeated selfing and selection, producing many new genetic combinations. Another method used to develop new, unique and superior tomato inbred lines and hybrids occurs when the breeder selects and crosses two or more parental lines followed by haploid induction and chromosome doubling that result in the development of dihaploid inbred lines. The breeder can theoretically generate billions of different genetic combinations via crossing, selfing and mutations and the same is true for the utilization of the dihaploid breeding method.

During the development of new tomato inbreds and hybrids, the tomato breeder uses tomato plants, but also non-commercial tomato plants, such as plants that may contain characteristics that the breeder has interest in having in its tomato inbreds and hybrids. Such non-commercial tomato plants could be wild relatives of tomato species.

Each year, the plant breeder selects the germplasm to advance to the next generation. This germplasm is grown under unique and different geographical, climatic and soil conditions, and further selections are then made, during and at the end of the growing season. The inbred lines developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines the breeder develops, except possibly in a very gross and general fashion. This unpredictability results in the expenditure of large research monies to develop superior new tomato inbred lines and hybrids.

The development of commercial tomato hybrids requires the development of homozygous inbred lines, the crossing of these lines, and the evaluation of the hybrid crosses.

Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i. Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential use as parents of new hybrid cultivars. Similarly, the development of new inbred lines through the dihaploid system requires the selection of the best inbreds followed by two to five years of testing in hybrid combinations in replicated plots.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more fruit containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each fruit by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

ii. Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of recurrent parent and the trait of interest from the donor parent are selected and repeatedly crossed (backcrossed) to the recurrent parent. The resulting plant is expected to have the attributes of the recurrent parent (e.g., cultivar) and the desirable trait transferred from the donor parent.

When the term hybrid tomato plant is used in the context of the present disclosure, this also includes any hybrid tomato plant where one or more desired traits have been introduced through backcrossing methods, whether such trait is derived from a naturally occurring one, a simultaneously or artificially-induced mutations, a transgenic one or a gene or a nucleotide sequence modified by the use of New Breeding Techniques. Backcrossing methods can be used with the present disclosure to improve or introduce one or more characteristic into the inbred parental line, thus potentially introducing these traits into the hybrid tomato plant of the present disclosure. The term "backcrossing" as used herein refers to the repeated crossing of a hybrid progeny back to the recurrent parent, i.e., backcrossing one, two, three, four, five, six, seven, eight, nine, or more times to the recurrent parent. The parental tomato plant which contributes the gene or the genes for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol.

In a typical backcross protocol, the original inbred of interest (recurrent parent) is crossed to or by a second inbred (nonrecurrent parent) that carries the gene or genes of interest to be transferred. The resulting progeny from this cross are then crossed again to or by the recurrent parent and the process is repeated until a tomato plant is obtained wherein all of the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact, the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the orange fruit color characteristic in tomato, requires selfing the progeny or using molecular markers to determine which plant carry the recessive allele(s).

Many single gene traits have been identified that are not regularly selected for in the development of a new parental inbred of a hybrid tomato plant according to the disclosure but that can be improved by backcrossing techniques. Single gene traits may or may not be transgenic. Examples of these traits include but are not limited to, male sterility (such as the ms1, ms2, ms3, ms4 or ms5 genes), herbicide resistance (such as bar or PAT genes), resistance for bacterial, fungal (genes Cf for resistance to *Cladosporium fulvum*) or viral disease (gene Ty for resistance to Tomato Yellow Leaf Curl Virus (TYLCV), genes Tm-1, Tm-2 and Tm22 for the resistance to the tomato mosaic tobamovirus (ToMV)), insect resistance (gene Mi for resistance to nematodes), increased brix by introduction of specific alleles such as the hir4 allele from *Lycopersicon hirsutum*, high lycopene by using the dg mutant as described in U.S. Ser. No. 10/587, 789, improved shelf life by using mutants such as the rin (ripening inhibitor), nor (non-ripening) or cnr (colorless non ripening) alleles, increased firmness or slower softening of the fruits due, for example in a mutation in an expansin gene, absence of gel (i.e. fruits having a cavity area which is solid and lacks a gel or liquid content male) by the use of the PSAF allele, fertility, enhanced nutritional quality, enhanced sugar content, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc., *Principles of Plant Breeding*). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly or essentially the same adaptation, yielding ability and quality characteristics of the recurrent parent but superior to that parent in the particular characteristic(s) for which the improvement program was undertaken. Therefore, this method provides the plant breeder with a high degree of genetic control of this work.

The method is scientifically exact because the morphological and agricultural features of the improved variety could be described in advance and because a similar variety could, if it were desired, be bred a second time by retracing the same steps (Briggs, "Breeding wheats resistant to bunt by the backcross method", 1930 *Jour. Amer. Soc. Agron.*, 22:289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be theoretically modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred or when using molecular markers that can identify the trait of interest.

The backcross technique is not only desirable when breeding for disease resistance but also for the adjustment of morphological characters, color characteristics and simply inherited quantitative characters such as earliness, plant height and seed size and shape.

ii. Open-Pollinated Populations

The improvement of open-pollinated populations of such crops as rye, maize and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagable by random-mating within itself in isolation.

Second, the synthetic variety attains the same end result as population improvement, but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc.

(1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by intercrossing a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops, including corn (maize), sorghum, sugarbeet, sunflower, broccoli and tomato as well as leafy vegetables such as lettuce. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Hybrid commercial tomato seed can be produced by controlled hand pollination. The male flowers from the male plants are harvested and used to pollinate the stigmatic surface of the female flowers on the female plants. Prior to, and after hand pollination, flowers are covered so that insects do not bring foreign pollen and create a mix or impurity. Flowers are tagged to identify pollinated fruit from which seed will be harvested.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA,* 99:9828-9832) and Quarrie et al. (Quarrie et al., 1999, *Journal of Experimental Botany,* 50 (337): 1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. In some embodiments, the donor or recipient female parent line and the donor or recipient male parent line are planted in the same greenhouse. The inbred male parent can be planted earlier than the female parent to ensure adequate pollen supply at the pollination time. In some embodiments, the male parent and female parent can be planted at a ratio of 1 male parent to 4-10 female parents. The male parent may be planted at the top of the field for efficient male flower collection during pollination. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. In some embodiments, this process is best done in the afternoon. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked fruits are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Breeding of dioecious species can also be done by growing equal amount of each parent plant. Insects are placed in the field or greenhouses for transfer of pollen from the male parent to the female flowers of the female parent. In some embodiments, fruits set after the introduction of the beehives can be marked for later collection.

viii. Targeting Induced Local Lesions in Genomes (TILL-ING)

Breeding schemes of the present application can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEco-TILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke a shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*, Fred Hutchinson Cancer Research, focusing on *Arabidopsis*; Southern Illinois University (USA), focusing on Soybean; John Innes Centre (UK), focusing on Lotus and *Medicago*; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus, in some embodiments, the breeding methods of the present disclosure include breeding with one or more TILLING plant lines with one or more identified mutations.

ix. Mutation Breeding

Mutation breeding is another method of introducing new variation and subsequent traits into tomato plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of engineered nucleases to enhance the efficacy and precision of gene editing in combination with oligonucleotides including, but not limited to Zinc Finger Nucleases (ZFN), TAL effector nucleases (TALENs), chemical nucleases, meganucleases, homing nucleases and clustered regularly interspaced short palindromic repeats (CRISPR)-associated endonuclease Cas (CRISPR-Cas) system (using such as Cas9, Cas12a/Cpf1, Cas13/C2c2, CasX and CasY) shall also be used to generate genetic variability and introduce new traits into tomato varieties.

x. Double Haploids and Chromosome Doubling

One way to obtain homozygous plants without the need to cross two parental lines followed by a long selection of the segregating progeny, and/or multiple backcrossing is to produce haploids and then double the chromosomes to form doubled haploids. Haploid plants can occur spontaneously, or may be artificially induced via chemical treatments or by crossing plants with inducer lines (Seymour et al. 2012, PNAS vol. 109, pg. 4227-4232; Zhang et al., 2008 Plant Cell Rep. December 27 (12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg. 63-72; Doubled Haploid Production in Crop Plants 2003 edited by Maluszynski ISBN 1-4020-1544-5). The production of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

xi. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xii. Embryo Rescue

Alternatively, embryo rescue may be employed in the transfer of resistance-conferring genomic material from a donor plant to a recipient plant. Embryo rescue can be used as a procedure to isolate embryos from crosses to rapidly move to the next generation of backcrossing or selfing or wherein plants fail to produce viable seed. In this process, the fertilized ovary or immature seed of a plant is tissue cultured to create new plants (see Pierik, 1999, In Vitro Culture of Higher Plants, Springer, ISBN 079235267X, 978-0792352679, which is incorporated herein by reference in its entirety).

Gene Editing/Genome Editing

Gene editing (or Genome editing) technologies. Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENs, CRISPR-Cas, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring tomato plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENs are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450,471; 8,586,526; 8,586,363; 8,592,645; 8,697,853; 8,704,041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et. al., Nat Rev Microbiol. 2011 May 9; 9(6): 467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

Plant Transformation

Tomato plants of the present disclosure, such as 'RED CORAL' can be further modified by introducing one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 U.S. application No. 20040197909) and also for bacterial and animal transformation (Kaepler et al., 1992; Raloff, 1990; Wang, 1995).

There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767, 378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19:259-268 (1982); Bevan et al., Nature 304:184-187 (1983)). However, many different antibiotics and antibiotic resistance genes can be used for transformation purposes (U.S. Pat. Nos. 5,034,322, 6,174, 724 and 6,255,560). In addition, several herbicides and herbicide resistance genes have been used for transformation purposes, including the bar gene, which confers resistance to the herbicide phosphinothricin (White et al., Nucl Acids Res 18:1062 (1990), Spencer et al., Theor Appl Genet 79:625-631 (1990), U.S. Pat. Nos. 4,795,855, 5,378,824 and 6,107, 549). In addition, the dhfr gene, which confers resistance to the anticancer agent methotrexate, has been used for selection (Bourouis et al., EMBO J. 2 (7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General genetic transformation methods, and specific methods for transforming certain plant species (e.g., maize) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming tomato plants and tomato tissue culture methods are described in McCormick, S. (Transformation of Tomato With *Agrobacterium tumefaciens*," Plant Tissue Culture Manual B6:1-9 (Kluwer Academic Publishers 1991)); and U.S. Pat. No. 5,569,831, each of which is herein incorporated by reference in its entirety for all purposes. The transformation can be physical, chemical and/or biological.

Grafting

Grafting is a process that has been used for many years in crops such as *cucurbitacea*, but only more recently for some commercial watermelon and tomato production. Grafting may be used to provide a certain level of resistance to telluric pathogens such as *Phytophthora* or to certain nematodes. Grafting is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases. In some recent developments, it has also been shown that some rootstocks are also able to improve the agronomic value for the grafted plant and in particular the equilibrium between the vegetative and generative development that are always difficult to balance in tomato cultivation.

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In some embodiments, the plants are selected on the basis of one or more phenotypic traits. Skilled persons will readily appreciate that such traits include any observable characteristic of the plant, including for example growth rate, vigor, plant health, maturity, branching, plant height, leaf coverage, weight, total yield, color, taste, sugar levels, aroma, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (fruit) or biomass production; effects on plant growth that results in an increased seed yield for a crop; effects on plant growth which result in an increased yield; effects on plant growth that lead to an increased resistance or tolerance to disease including fungal, viral or bacterial diseases, to *mycoplasma*, or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of tomato exocarp (skin) of said fruit.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Whole Transcriptome Shotgun Sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, Radioimmune Assay (RIA), immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene, or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR. An exemplary PCR scheme is presented below.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 60° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. This combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

For example, the real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLID, Illumina GA/HiSeq, Ion PGM, Mi Seq, among others (Liu et al., 2012 Journal of Biomedicine and Biotechnology Volume 2012 ID 251364; Franca et al., 2002 Quarterly Reviews of Biophysics 35 pg. 169-200; Mardis 2008 Genomics and Human Genetics vol. 9 pg. 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments, said donor plants contain a gene or genes of interest which may confer the plant with a desirable phenotype. The recipient line can be an elite line having certain favorable traits for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R.G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait(s) into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.;* 2(10):e245).

Tissue Culture

As it is well known in the art, tissue culture of tomato can be used for the in vitro regeneration of tomato plants. Tissues cultures of various tissues of tomato and regeneration of plants therefrom are well known and published. By way of example, a tissue culture comprising organs has been used to produce regenerated plants as described in Girish-Chandel et al., Advances in Plant Sciences. 2000, 13:1, 11-17, Costa et al., Plant Cell Report. 2000, 19:3327-332, Plastira et al., Acta Horticulturae. 1997, 447, 231-234, Zagorska et al., Plant Cell Report. 1998, 17:12 968-973, Asahura et al., Breeding Science. 1995, 45:455-459, Chen et al., Breeding Science. 1994, 44:3, 257-262, Patil et al., Plant and Tissue and Organ Culture. 1994, 36:2, 255-258. It is clear from the literature that the state of the art is such that these methods of obtaining plants are routinely used and have a very high rate of success. Thus, another aspect of this disclosure is to provide cells which upon growth and differentiation produce tomato plants having all of the physiological and morphological characteristics of hybrid tomato plant RED CORAL.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollens, flowers, seeds, leaves, stems, roots, root tips, anthers, pistils, meristematic cells, axillary buds, ovaries, seed coats, endosperms, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Example 1—Development of New RED CORAL Tomato Variety

Breeding History of RED CORAL

Hybrid tomato plant RED CORAL has superior characteristics. The female (TOM3828PL) and male (TOM3971PL) parents were crossed to produce hybrid (F1) seeds of RED CORAL. The seeds of RED CORAL can be grown to produce hybrid plants and parts thereof. The hybrid RED CORAL can be propagated by seeds produced from crossing tomato inbred line TOM3828PL with tomato inbred line TOM3971PL or vegetatively.

The origin and breeding history of hybrid plant RED CORAL can be summarized as follows: the line TOM3828PL was used as the female plant and crossed by pollen from the line TOM3971PL (both proprietary lines owned by HM.CLAUSE, Inc.). The first trial planting of this hybrid was done in Immokalee-FL in the first year, followed by trials in Parrish-FL, Davis-CA, as well as Immokalee-FL for six additional years. An example of such trial being disclosed in Tables 2 and 3.

The inbred line TOM3828PL is a parent with small plant architecture, relatively open vine, concentrated maturity, and high quality fruits with slightly elongated fruit shape. This inbred line was used as female parent in this cross.

The inbred TOM3971PL is a parent with strong vine and multiparous inflorescence. Fruits are firm, with dark red color and slightly elongated fruit shape. It was used as the male parent in this cross.

Hybrid tomato plant RED CORAL is similar to hybrid tomato RUBY CRUSH, a commercial variety. As shown in Tables 1, 2 and 3, while similar to hybrid tomato RUBY CRUSH, there are significant differences including the sugar content, which is higher for RED CORAL. Fruits of RED CORAL are smaller, displaying higher firmness and uniformity as compared to RUBY CRUSH. Also, hybrid tomato plant RED CORAL shows Resistance to Tomato yellow leaf curl virus (TYLCV) and Resistance to Tomato spotted wilt virus (TSWV)-Race 0 whereas these resistances are absent in RUBY CRUSH.

Some of the criteria used to select the hybrid RED CORAL as well as their inbred parent lines in various generations include: plant architecture, fruit firmness, fruit shape, sugar content, as well as disease resistances. Additionally, fruit yield and sugar content were used to select the hybrid.

Hybrid tomato plant RED CORAL has shown uniformity and stability for the traits, within the limits of environmental influence for the traits as described in the following Variety Descriptive Information. No variant traits have been observed or are expected for important horticultural traits in tomato hybrid RED CORAL.

Hybrid tomato plant RED CORAL has the following morphologic and other characteristics, as compared to RUBY CRUSH (based primarily on data collected in Davis, California, and Parrish, Florida, USA, all experiments done under the direct supervision of the applicant) (Table 1).

TABLE 1

| | | Phenotypic descriptions of RED CORAL | | | |
|---|---|---|---|---|---|
| | | Trait | Scale | RED CORAL | RUBY CRUSH |
| | | Plant | | | |
| 1 | | Seed-propagated varieties only: Seedling: Anythocyanin coloration of hypocotyl | absent, present | present | present |

TABLE 1-continued

Phenotypic descriptions of RED CORAL

| | Trait | Scale | RED CORAL | RUBY CRUSH |
|---|---|---|---|---|
| 2 | Plant: Growth type | determinate, indeterminate | determinate | determinate |
| 3 | Only determinate varieties: Plant: Number of inflorescence on main stem | few, medium, many | medium | many |
| 4 | Stem: anythocyanin coloration | absent or very weak, weak, medium, strong, very strong | absent or very weak | absent |
| 5 | Only indeterminate varieties: Stem: Length of internode | short, medium, long | n/a | n/a |
| 6 | Only indeterminate varieties: Plant: Height | very short, short, medium, long, very long | n/a | n/a |

Leaf

| | | | | |
|---|---|---|---|---|
| 7 | Leaf: Attitude | erect, semi-erect, horizontal, semi-drooping, drooping | semi-erect | demi-drooping |
| 8 | Leaf: Length | short, medium, long | medium | medium |
| 9 | Leaf: Width | narrow, medium, broad | medium | broad |
| 10 | Leaf: Type of blade | pinnate, bipinnate | bipinnate | bipinnate |
| 11 | Leaf: Size of leaflets | very small, small, medium, large, very large | small | small |
| 12 | Leaf: Intensity of green color | light, medium, dark | medium | medium |
| 13 | Leaf: Glossiness | weak, medium, strong | weak | weak |
| 14 | Leaf: Blistering | weak, medium, strong | medium | strong |
| 15 | Leaf: Attitude of petiole of leaflet in relation to main axis | semi-erect, horizontal, semi-drooping | horizontal | semi-erect |

Inflorescence

| | | | | |
|---|---|---|---|---|
| 16 | Inflorescence: Type | mainly uniparous, equally uniparous and multiparous, mainly multiparous | equally uniparous and multiparous | equally uniparous and multiparous |
| 17 | Flower: Color | yellow, orange | yellow | yellow |
| 18 | Flower: Pubescence of style | absent, present | present | absent |

Fruit

| | | | | |
|---|---|---|---|---|
| 19 | Peduncle: abscission layer | absent, present | present | present |
| 20 | Only varieties with peduncle abscission layer: Pedicel length | short, medium, long | medium | medium |
| 21 | Fruit: Green shoulder (before maturity) | absent, present | absent | absent |
| 22 | Fruit: Extent of green shoulder (before maturity) | very small, small, medium, large | very small | very small |
| 23 | Fruit: Intensity of green color of shoulder (before maturity) | light, medium, dark | light | light |
| 24 | Fruit: Intensity of green color excluding shoulder (before maturity) | very light, light, medium, dark, very dark | very light | very light |
| 25 | Fruit: Green stripes (before maturity) | absent, present | absent | absent |
| 26 | Fruit: Size | very small, small, medium, large, very large | very small | small |
| 27 | Fruit: Ratio length/diameter | very compressed, moderately compressed, medium, moderately elongated, very elongated | moderately elongated | moderately elongated |
| 28 | Fruit: Shape in longitudinal section | flattened, oblate, circular, oblong, cylindric, elliptic, cordate, ovate, obovate, pyriform, obcordate | obovate | obovate |
| 29 | Fruit: Ribbing at peduncle end | absent or very weak, weak, medium, strong, very strong | absent or very weak | absent or very weak |

TABLE 1-continued

Phenotypic descriptions of RED CORAL

| | Trait | Scale | RED CORAL | RUBY CRUSH |
|---|---|---|---|---|
| 30 | Fruit: Depression at peduncle end | absent or very weak, weak, medium, strong | absent or very weak | absent or very weak |
| 31 | Fruit: Size of peduncle scar | very small, small, medium, large, very large | very small | very small |
| 32 | Fruit: Size of blossom scar | very small, small, medium, large, very large | very small | n/a |
| 33 | Fruit: Shape at blossom end | indented, indented to flat, flat, flat to pointed, pointed | flat | flat |
| 34 | Fruit: Diameter of core in cross section in relation to total diameter | very small, small, medium, large, very large | very small | very small |
| 35 | Fruit: Thickness of pericarp | very thin, thin, medium, thick, very thick | thin | thin |
| 36 | Fruit: Number of locules | only two; two and three; three and four; four, five, or six; more than six | 2 | 2 |
| 37 | Fruit: Color at maturity | cream, yellow, orange, pink, red, brown, green | red | red |
| 38 | Fruit: Color of flesh (at maturity) | cream, yellow, orange, pink, red, brown, green | red | red |
| 39 | Fruit: Glossiness of skin | weak, medium, strong | medium | medium |
| 40 | Fruit: Color of epidermis | colorless, yellow | yellow | yellow |
| 41 | Fruit: Firmness | very soft, soft, medium, firm, very firm | medium | soft |
| 42 | Fruit: Shelf-life | very short, short, medium, long, very long | medium | medium |
| | | Additional traits | | |
| 43 | Time of flowering | early, medium, late | early | medium |
| 44 | Time of maturity | very early, early, medium, late, very late | early | medium |
| 45 | Sensitivity to silvering | insensitive, sensitive | insensitive | insensitive |
| | | Disease Resistance | | |
| 46 | Resistance to *Meloidogyne incognita* (Mi) | susceptible, moderately resistant, highly resistant | moderately resistant | absent |
| 47 | Resistance to *Verticillium* sp. (Va and Vd) - Race 0 | absent, present | present | absent |
| 48.1 | Resistance to *Fusarium oxysporum* f. sp. *lycopersici* (Fol) - Race 0 (ex 1) | absent, present | present | present |
| 48.2 | Resistance to *Fusarium oxysporum* f. sp. *lycopersici* (Fol) - Race 1 (ex 2) | absent, present | present | present |
| 48.3 | Resistance to *Fusarium oxysporum* f. sp. *lycopersici* (Fol) - Race 2 (ex 3) | absent, present | absent | absent |
| 49 | Resistance to *Fusarium oxysporum* f. sp. *radicislycopersici* (Forl) | absent, present | absent | present |
| 50.1 | Resistance to *Fulvia fulva* (Ff) (ex *Cladosporium fulvum*) - Race 0 | absent, present | absent | absent |
| 50.2 | Resistance to *Fulvia fulva* (Ff) (ex *Cladosporium fulvum*) - Group A | absent, present | absent | absent |
| 50.3 | Resistance to *Fulvia fulva* (Ff) (ex *Cladosporium fulvum*) - Group B | absent, present | absent | absent |
| 50.4 | Resistance to *Fulvia fulva* (Ff) (ex *Cladosporium fulvum*) - Group C | absent, present | absent | absent |

TABLE 1-continued

Phenotypic descriptions of RED CORAL

| | Trait | Scale | RED CORAL | RUBY CRUSH |
|---|---|---|---|---|
| 50.5 | Resistance to *Fulvia fulva* (Ff) (ex *Cladosporium fulvum*) - Group D | absent, present | absent | absent |
| 50.6 | Resistance to *Fulvia fulva* (Ff) (ex *Cladosporium fulvum*) - Group E | absent, present | absent | absent |
| 51.1 | Resistance to Tomato mosaic virus (ToMV) - Strain 0 | absent, present | absent | present |
| 51.2 | Resistance to Tomato mosaic virus (ToMV) - Strain 1 | absent, present | absent | present |
| 51.3 | Resistance to Tomato mosaic virus (ToMV) - Strain 2 | absent, present | absent | present |
| 52 | Resistance to *Phytophthora infestans* (Pi) | absent, present | absent | absent |
| 53 | Resistance to *Pyrenochaeta lycopersici* (Pl) | absent, present | absent | absent |
| 54 | Resistance to *Stemphylium* spp. (Ss) | absent, present | absent | present |
| 55 | Resistance to *Pseudomonas syringae* pv. tomato (Pst) | absent, present | present | absent |
| 56 | Resistance to *Ralstonia solanacearum* (Rs) - Race 1 | absent, present | absent | absent |
| 57 | Resistance to Tomato yellow leaf curl virus (TYLCV) | absent, present | present | absent |
| 58 | Resistance to Tomato spotted wilt virus (TSWV) - Race 0 | absent, present | present | absent |
| 59 | Resistance to *Leveillula taurica* (Lt) | absent, present | absent | absent |
| 60 | Resistance to *Oidium neolycopersici* (On) (ex *Oidium lycopersicum* (Ol)) | absent, present | absent | absent |
| 61 | Resistance to Tomato torrado virus (ToTV) | absent, present | absent | absent |

Example 2—Comparison of New RED CORAL Tomato with Check Variety

In the tables that follow (Tables 2 and 3) the traits and characteristics of hybrid tomato plant RED CORAL are given compared to another hybrid, the variety RUBY CRUSH. The data was collected are presented for key characteristics and traits. Hybrid tomato RED CORAL was tested during multiple growing periods in a single year from several field locations, with two or more replications per location. Information about the hybrid, as compared to a check hybrid is presented (based primarily on data collected in California). All experiments were done under the direct supervision of the applicant).

TABLE 2

Horticultural and yield performance of RED CORAL compared to commercial check RUBY CRUSH in Parrish, Florida, USA. Trial planted on August 17$^{th}$ Year 1 and evaluated on November 10$^{th}$ Year 1

| Hybrid | VN | CV | FRM | SHP | COL | UNI | FW | AFW | A B |
|---|---|---|---|---|---|---|---|---|---|
| RED CORAL | 5 | 4 | 5 | 6 | 5 | 6 | 374 | 7.48 | 7.7 |
| RUBY CRUSH | 5 | 5 | 4 | 5 | 6 | 5 | 536 | 10.72 | 6.4 |

VN = Vine vigor, CV = fruit cover, FRM = fruit firmness, SHP = fruit shape, COL = fruit color, UNI = fruit uniformity, A F W = average fruit weight (grams) in a 50-fruit sample, A B = average sugar content (brix) from five measurements using portable brix meter refractometer.

Traits VN, CV, FRM, COL, and UNI were quantified using a 1 to 9 scale, with 1 being the worse and 9 being the best.

SHP was quantified using a 1 to 9 scale, where 1 = flat, 2 = round, 3 = deep round, 4 = blocky, 5 = blocky grape, 6 = grape, 7 = elongated grape, 8 = very elongated grape, 9 extreme elongated grape

TABLE 3

Horticultural and yield performance of RED CORAL compared to commercial check RUBY CRUSH in Parrish, Florida, USA. Trial planted on Feb 23$^{rd}$ Year 2 and evaluated on May 9$^{th}$ Year 2

| Hybrid | VN | CV | FRM | SHP | COL | UNI | AF W | A B |
|---|---|---|---|---|---|---|---|---|
| RED CORAL | 6 | 6 | 7 | 7 | 6 | 7 | 9.5 | 7.24 |
| RUBY CRUSH | 6 | 6 | 6 | 5 | 5 | 6 | 13.56 | 6.6 |

VN = Vine vigor, CV = fruit cover, FRM = fruit firmness, SHP = fruit shape, COL = fruit color, UNI = fruit uniformity, A F W = average fruit weight (grams) in a 50-fruit sample, A B = average sugar content (brix) from five measurements using portable brix meter refractometer.
Traits VN, CV, FRM, COL, and UNI were quantified using a 1 to 9 scale, with 1 being the worse and 9 being the best.
SHP was quantified using a 1 to 9 scale, where 1 = flat, 2 = round, 3 = deep round, 4 = blocky, 5 = blocky grape, 6 = grape, 7 = elongated grape, 8 = very elongated grape, 9 extreme elongated grape

DEPOSIT INFORMATION

A deposit of the tomato seed of this disclosure is maintained by HM.CLAUSE, Inc. Davis Research Station, 9241 Mace Boulevard, Davis, California 95618. In addition, a sample of the hybrid tomato seed of this disclosure has been deposited with the National Collections of Industrial, Food and Marine Bacteria (NCIMB), NCIMB Ltd. Ferguson Building, Craibstone Estate, Bucksburn, Aberdeen, AB21 9YA Scotland.

To satisfy the enablement requirements of 35 U.S.C. 112, and to certify that the deposit of the isolated strain of the present disclosure meets the criteria set forth in 37 CFR 1.801-1.809, Applicants hereby make the following statements regarding the deposited hybrid tomato RED CORAL (deposited as NCIMB Accession No. 44216 on Aug. 31, 2023).

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A tomato plant, a part thereof, or a cell thereof, produced by growing seed of hybrid tomato designated RED CORAL wherein a representative sample of said seed has been deposited under NCIMB No. 44216, wherein the tomato plant has all of the physiological and morphological characteristics of hybrid tomato designated RED CORAL when grown under the same environmental condition.

2. The tomato plant, the part thereof, or the cell thereof of claim 1, wherein the part is selected from the group consisting of a leaf, a flower, a fruit, a stalk, a root, a rootstock, a scion, a meristem, and a cell.

3. A tissue culture of regenerable cells produced from the tomato plant or the part thereof of claim 1, wherein a tomato plant regenerated from the tissue culture has all of the physiological and morphological characteristics of hybrid tomato designated RED CORAL when grown under the same environmental condition.

4. A tomato plant regenerated from the tissue culture of claim 3, wherein the tomato plant has all of the physiological and morphological characteristics of hybrid tomato designated RED CORAL when grown under the same environmental condition.

5. A method for harvesting a tomato fruit, the method comprising: (a) growing the tomato plant of claim 1 to produce a tomato fruit, and (b) harvesting said tomato fruit.

6. A method for producing a tomato seed, the method comprising: (a) crossing a first tomato plant with a second tomato plant and (b) harvesting the resultant tomato seed, wherein said first tomato plant and/or second tomato plant is the tomato plant of claim 1.

7. A method for producing a tomato seed, the method comprising: (a) self-pollinating the tomato plant of claim 1 and (b) harvesting the resultant tomato seed.

8. A method of vegetatively propagating a tomato plant, the method comprising: (a) collecting a part capable of being propagated from the plant of claim 1 and (b) regenerating a plant from said part.

9. The method of claim 8, further comprising (c) harvesting a fruit from said regenerated plant.

10. A plant obtained from the method of claim 8, wherein said plant has all of the physiological and morphological characteristics of hybrid tomato designated RED CORAL deposited under NCIMB No. 44216.

11. A tomato fruit selected from the group consisting of: (a) a tomato fruit produced from the plant of claim 1; (b) a tomato fruit produced by the method of claim 6, and (c) a tomato fruit produced from the method of claim 9.

12. A method of producing a tomato plant obtained from hybrid tomato designated RED CORAL, the method comprising: (a) self-pollinating the tomato plant of claim 1 at least once to produce a progeny tomato plant obtained from hybrid tomato designated RED CORAL.

13. The method of claim 12, further comprising the steps of:
  (b) crossing the progeny tomato plant obtained from the hybrid tomato designated RED CORAL with itself or a second tomato plant to produce a progeny seed of a subsequent generation;
  (c) growing a progeny plant from the progeny seed of the subsequent generation;
  (d) crossing the progeny plant of the subsequent generation with itself or a second tomato plant to produce a tomato plant derived from the hybrid tomato designated RED CORAL; and
  (e) repeating step (c) and (d) for at least one generation to produce a tomato plant further derived from the hybrid tomato designated RED CORAL.

14. A method of producing a tomato plant obtained from hybrid tomato designated RED CORAL, the method comprising: (a) crossing the tomato plant of claim 1 with a second tomato plant to produce a progeny tomato plant obtained from hybrid tomato designated RED CORAL.

15. The method of claim 14, further comprising the steps of:
  (b) crossing the progeny tomato plant obtained from the hybrid tomato plant designated RED CORAL with itself or a second tomato plant to produce a progeny seed of a subsequent generation;
  (c) growing a progeny plant from the progeny seed of the subsequent generation;
  (d) crossing the progeny plant of the subsequent generation with itself or a second tomato plant to produce a tomato plant derived from the hybrid tomato plant designated RED CORAL; and
  (e) repeating step (c) and (d) for at least one generation to produce a tomato plant further derived from the hybrid tomato plant designated RED CORAL.

16. A method of producing a plant of hybrid tomato designated RED CORAL comprising at least one desired trait, the method comprising introducing a single locus conversion conferring the desired trait into a cell of a hybrid tomato plant designated RED CORAL, whereby a plant of hybrid tomato designated RED CORAL comprising the desired trait is produced, wherein a representative sample of seed of said hybrid has been deposited under NCIMB No. 44216.

17. A tomato plant, a part thereof, or a cell thereof, produced by the method of claim 16, wherein the single locus conversion is introduced into the plant by genetic transformation or a genome editing technique, and wherein the plant, the part, or the cell thereof comprises single locus conversion and otherwise all of the physiological and morphological characteristics of hybrid tomato plant RED CORAL.

18. The plant of claim 17, wherein the single locus conversion confers said plant with male sterility, male fertility, herbicide resistance, insect resistance, disease resistance, water stress tolerance, heat tolerance, improved standability, enhanced plant vigor, improved shelf life, delayed senescence or controlled ripening, and/or increased nutritional quality.

19. The plant of claim 18, wherein the single locus conversion is introduced into the plant by a genome editing technique with a nuclease selected from the group consisting of Zinc finger nuclease (ZFN), Transcription Activation-Like Effector Nuclease (TALEN), Clustered Regularly Interspaced Short Palindromic Repeats-associated Cas endonuclease (CRISPR-Cas), meganuclease, homing endonuclease, and RNA-guided nuclease.

20. A method of producing a tomato plant, the method comprising: grafting a rootstock or a scion of the hybrid tomato plant of claim 2 to another tomato plant.

21. A method for producing nucleic acids for breeding and analysis, the method comprising: isolating nucleic acids from the plant of claim 2, a part, or a cell thereof.

22. A method for producing a second tomato plant, the method comprising applying plant breeding techniques to the plant or part of claim 1 to produce the second tomato plant.

23. A method of producing a commodity plant product, the method comprising obtaining the plant of claim 1 or a part thereof and producing said commodity plant product therefrom.

\* \* \* \* \*